US00PP28887P2

(12) United States Plant Patent
Dirr et al.

(10) Patent No.: US PP28,887 P2
(45) Date of Patent: Jan. 23, 2018

(54) ***ILLICIUM* PLANT NAMED 'PIIIP-I'**

(50) Latin Name: *Illicium parviflorum*
Varietal Denomination: PIIIP-I

(71) Applicant: Bailey Nurseries, Inc., Newport, MN (US)

(72) Inventors: Michael A. Dirr, Bogart, GA (US); Joshua H. Kardos, Asheville, NC (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 15/330,386

(22) Filed: Sep. 13, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Penny J. Aguirre

(57) ABSTRACT

A new cultivar of *Illicium* plant named, 'PIIIP-I', that is characterized by its evergreen, compact, mounding growth habit, its foliage that is yellow-green in color in the summer, its foliage that is yellow in color in the winter, and its flowers that are yellow in color.

2 Drawing Sheets

Botanical classification: *Illicium parviflorum.*
Cultivar designation: 'PIIIP-I'.

BACKGROUND OF THE INVENTION

The present invention relates to a new and distinct cultivar of *Illicium parviflorum*, botanically known as *Illicium* 'PIIIP-I' and will be referred to hereafter by its cultivar name, 'PIIIP-I'. 'PIIIP-I' represents a new evergreen shrub grown for landscape use.

The new cultivar of *Illicium* arose from an ongoing breeding program conducted by the Inventors in Watkinsville, Ga. 'PIIIP-I' originated as a seedling that arose from seed planted from the open pollination of *Illicium parviflorum* 'Florida Sunshine' (not patented) in 2009. 'PIIIP-I' was selected as a single unique plant in 2011 from amongst the resulting seedlings.

Asexual propagation of the new cultivar was first accomplished by one of the Inventors using semi-hardwood cuttings in Watkinsville, Ga. in 2011. Asexual propagation by semi-hardwood cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'PIIIP-I' as a new and distinct cultivar of *Illicium.*

1. 'PIIIP-I' exhibits an evergreen, compact, mounding growth habit.
2. 'PIIIP-I' exhibits foliage that is yellow-green in color in the summer.
3. 'PIIIP-I' exhibits foliage that is yellow in color in the winter.
4. 'PIIIP-I' exhibits flowers that are yellow in color.

Plants of the new *Illicium* 'PIIIP-I' can be most closely compared to the female parent 'Florida Sunshine'. 'PIIIP-I' is distinguished from its female parent 'Florida Sunshine' primarily in growth habit. 'Florida Sunshine' has a more open and loser habit and is ultimately a taller plant, whereas 'PIIIP-I' has a tight, dense habit and is ultimately smaller in height than 'Florida Sunshine'.

Plants of the new *Illicium* 'PIIIP-I' can also be compared to typical plants of *Illicium parviflorum* (not patented), but differs in the following characteristics; 'PIIIP-I' has yellow-green foliage in the summer, whereas *Illicium parviflorum* has olive green foliage. 'PIIIP-I' is a plant that needs to be planted in the full shade, whereas *Illicium parviflorum* performs well not only in the full shade, but also the full sun.

Plants of the new *Illicium* 'PIIIP-I' can also be compared to its sister seedling known as 'YL-02-09' (not patented). 'PIIIP-I' has a tighter denser habit, whereas 'YL-02-09' is more like its female parent having a more open, loser habit in general and becoming much taller than 'PIIIP-I'. 'PIIIP-I' does not scorch as bad in the sun as 'YL-02-09'.

BRIEF DESCRIPTION OF THE DRAWINGS

The accompanying colored photographs illustrate the overall appearance and distinct characteristics of the new *Illicium*. The photographs were taken of six year-old plants of 'PIIIP-I' as grown in the ground in Watkinsville, Ga.

The photograph in FIG. 1 provides a side-view of the overall plant habit of 'PIIIP-I'.

Figure 1:
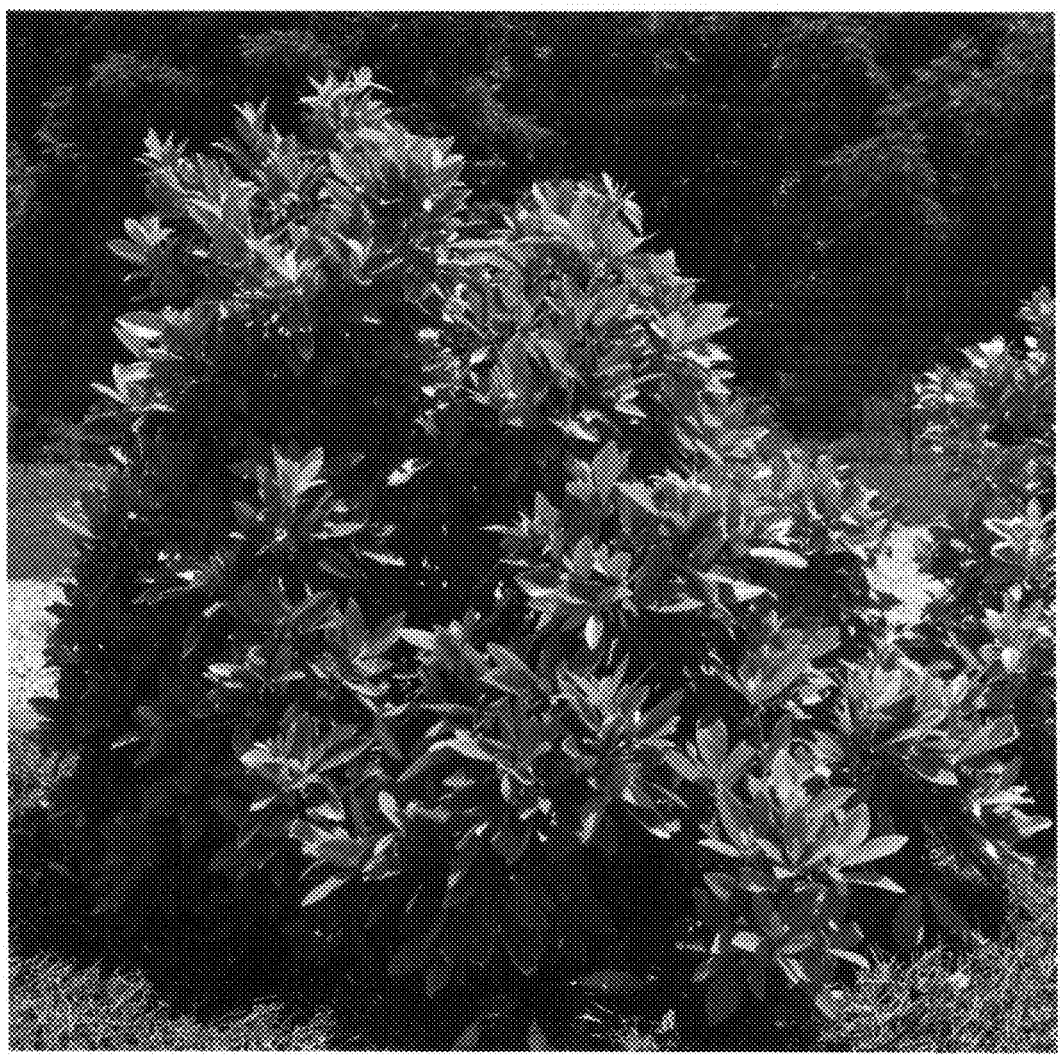
Figure 2:
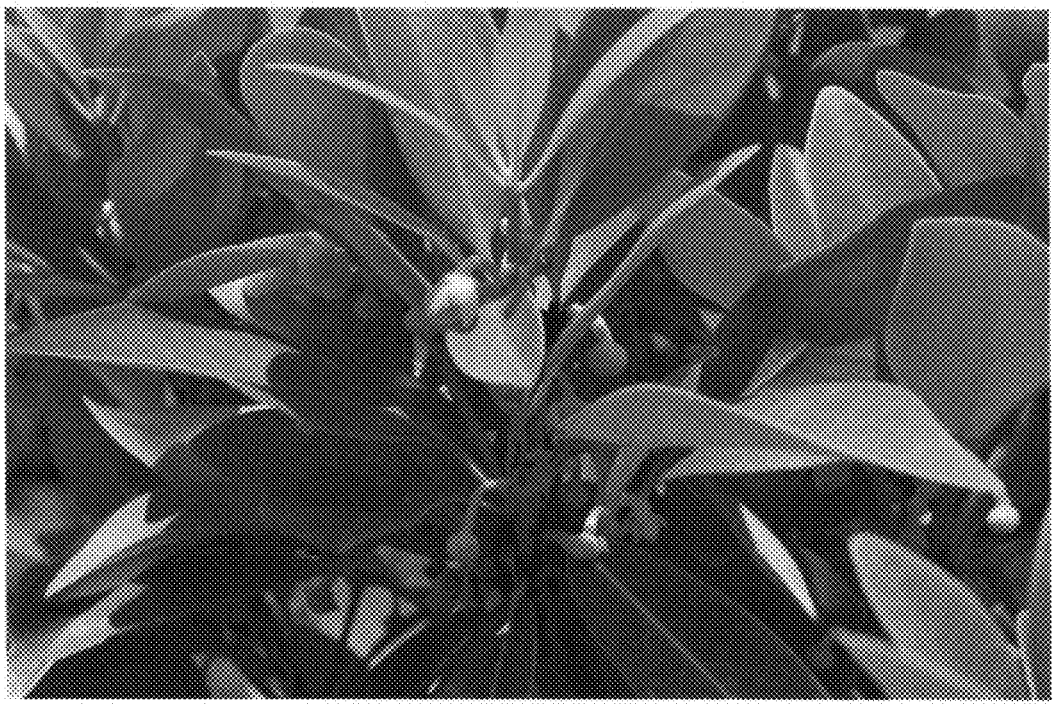

The photograph in FIG. 2 provides a close-up view of the flowers and foliage of 'PIIIP-I'.

The colors in the photographs are as close as possible with the photographic and printing technology utilized and the color values cited in the Detailed Botanical Description accurately describe the colors of the new *Illicium.*

DETAILED BOTANICAL DESCRIPTION OF THE PLANT

The following is a detailed description of six year-old plants of the new cultivar as grown in the ground under shade in Watkinsville, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—From June to August in Watkinsville, Ga.

*Plant type*.—Evergreen shrub.

*Plant habit*.—Freely branching, compact, mounding.

*Height and spread*.—An average of 46 cm in height and 81 cm in width as a 6 year-old plant in the landscape.

*Hardiness*.—At least in U.S.D.A. Zones 6 to 9.

*Diseases and pests*.—No susceptibility and resistance to diseases or pests as has been observed.

*Root description*.—Fibrous and fine when young, woody and 199C in color when older.

*Growth rate*.—Slow to moderate.

*Propagation*.—Semi-hard wood cuttings.

*Time required for root development*.—An average of six weeks for root initiation (at 32° C.) with a young plant produced in an average of 3 months (at 32° C.).

Branch description:

*Branch shape*.—Rounded.

*Branch color*.—New growth; 1C, mature branches; 199B.

*Stem size*.—35 to 81 cm in length and 1 cm in diameter.

*Stem surface*.—Smooth with coarse irregularly spotted with lenticels 199B in color.

*Branching*.—Moderately branched with an average of 12 lateral branches held at an average angle between 45° to 75°.

*Branch strength*.—Very strong.

Foliage description:

*Leaf shape*.—Elliptic.

*Leaf division*.—Simple.

*Leaf base*.—Cuneate.

*Leaf apex*.—Acute.

*Leaf venation*.—Pinnate, upper and lower surface color 1C.

*Leaf margins*.—Entire.

*Leaf attachment*.—Petiolate.

*Leaf arrangement*.—Pseudo-whorled, 6 to 8 leaves per terminal whorl.

*Leaf aspect*.—Young foliage held at an average angle of 40° to the lateral stem, mature foliage held at an average angle of 60° to the lateral stem.

*Leaf color*.—Young upper and lower surface; N144B, mature upper surface; N144C, mature lower surface; 145A, winter foliage upper surface; N144B, winter foliage lower surface; 145C.

*Leaf surface*.—Upper and lower surface smooth and leathery.

*Leaf size*.—An average of 8 cm in length and 3 cm in width.

*Leaf fragrance*.—Anise-like scent.

*Petioles*.—An average of 1.5 cm in length and 3 mm in width, 1B in color, glabrous surface.

*Stipules*.—Not present.

Flower description:

*Inflorescence type*.—An average of 3 rounded, solitary flowers occuring at axils of lateral branches.

*Lastingness of flowers*.—Persistent.

*Flower size*.—An average of 1.5 cm in length and 5 mm in diameter.

*Flower fragrance*.—Sweet, pleasant scent.

*Flower number*.—An average of 12 flowers per lateral branch occuring in groups of about 3 at leaf axils.

*Flower aspect*.—Nodding downwards.

*Flower buds*.—Rounded in shape, an average of 6 mm in length and 7 mm in diameter, 15B in color, glabrous and smooth surface.

*Petals*.—An average of 8, ovate in shape, arranged radially and slightly overlapping, glabrous and smooth on upper and lower surfaces, entire margins, obtuse apex, attenuate base, an average of 5 mm in length and 4 mm in width, color; upper surface 16A and lower surface 16B.

*Sepal*.—An average of 4, obovate in shape, glabrous and smooth on upper and lower surfaces, entire margins, obtuse apex, attenuate base, an average of 5 mm in length and 4 mm in width, upper and lower surfaces 1D in color.

*Peduncle*.—Rounded in shape, an average of 1 cm in length and 2.5 mm in diameter, smooth, glabrous surface, 149C in color, strong and curved downward.

*Pedicel*.—None.

Reproductive organs:

*Gynoecium*.—1 pistil, an average of 2 mm in length with style an average of 1 mm in length, 1D in color.

*Androcoecium*.—An average of 16 stamens, an average of 1 mm in length and less than 1 mm in width, 1D in color, anthers are minute and no pollen has been observed.

It is claimed:

1. A new and distinct cultivar of *Illicium* plant named 'PIIIP-I' as herein illustrated and described.

* * * * *